United States Patent [19]
Tilton, Jr.

[11] Patent Number: 5,919,184
[45] Date of Patent: *Jul. 6, 1999

[54] INSTRUMENTATION FOR LAPAROSCOPIC INSERTION AND APPLICATION OF SURGICAL SHEET MATERIAL

[76] Inventor: Eugene B. Tilton, Jr., 513 Dorrington Blvd, Metairie, La. 70005

[*] Notice: This patent issued on a continued prosecution application filed under 37 CFR 1.53(d), and is subject to the twenty year patent term provisions of 35 U.S.C. 154(a)(2).

[21] Appl. No.: 08/625,098

[22] Filed: Apr. 1, 1996

Related U.S. Application Data

[63] Continuation-in-part of application No. 08/407,409, Mar. 17, 1995, Pat. No. 5,503,623.

[51] Int. Cl.$^6$ .................................................. A61B 17/00
[52] U.S. Cl. ................................ 606/1; 606/151; 604/11; 604/27; 604/36; 604/158; 604/171; 604/264
[58] Field of Search ............................... 128/898; 600/37; 602/57; 604/1, 2, 11–15, 17, 18, 27, 36, 43–45, 47–51, 59–64, 158–166, 171, 203, 264; 606/1, 151

[56] References Cited

U.S. PATENT DOCUMENTS

| | | | |
|---|---|---|---|
| 5,125,910 | 6/1992 | Freitas | 604/249 |
| 5,257,973 | 11/1993 | Villasuso | 604/49 |
| 5,263,927 | 11/1993 | Shlain | 604/13 |
| 5,295,952 | 3/1994 | Pietrafitta | 604/15 |
| 5,304,187 | 4/1994 | Green et al. | 604/13 X |
| 5,310,407 | 5/1994 | Casale | 604/59 |
| 5,533,986 | 7/1996 | Mottola et al. | 604/264 |

*Primary Examiner*—Robert L. Nasser
*Attorney, Agent, or Firm*—Garvey, Smith, Nehrbass & Doody, L.L.C.

[57] ABSTRACT

A method and apparatus for laparoscopic insertion and application of a sheet like material (such as an adhesion barrier) and the like products enables the laparoscopic surgeon to utilize large and full size sheets of Interceed (3"×4") in abdominal (including pelvic) surgery. In laparoscopy surgery of the abdomen (including pelvis), all instrumentation and all surgical products must be introduced through "ports" consisting of valved sleeved or tubes. To properly and efficiently introduce and apply a large or full size sheet of sheet like material, the present invention provides a method and apparatus for grasping and furling the sheet and then unfurling, releasing and applying it after passage into the patient's abdominal cavity. The instrument consists of an operational grasping and furling portion which is rotated to furl the sheet like material. It is then "back-loaded" or drawn into a tubular portion of the instrument, an inserter sheath for passage through the valved "port". Once the sheet like material is in the abdominal cavity it is unfurled. The grasping portion of the instrument provides for proper and easier alignment and then application of the unfurled sheet. Additional flexibility is achieved by an articulation mechanism which allows horizontal movement of the grasping/furling element to produce an angle in the instrument body.

23 Claims, 8 Drawing Sheets

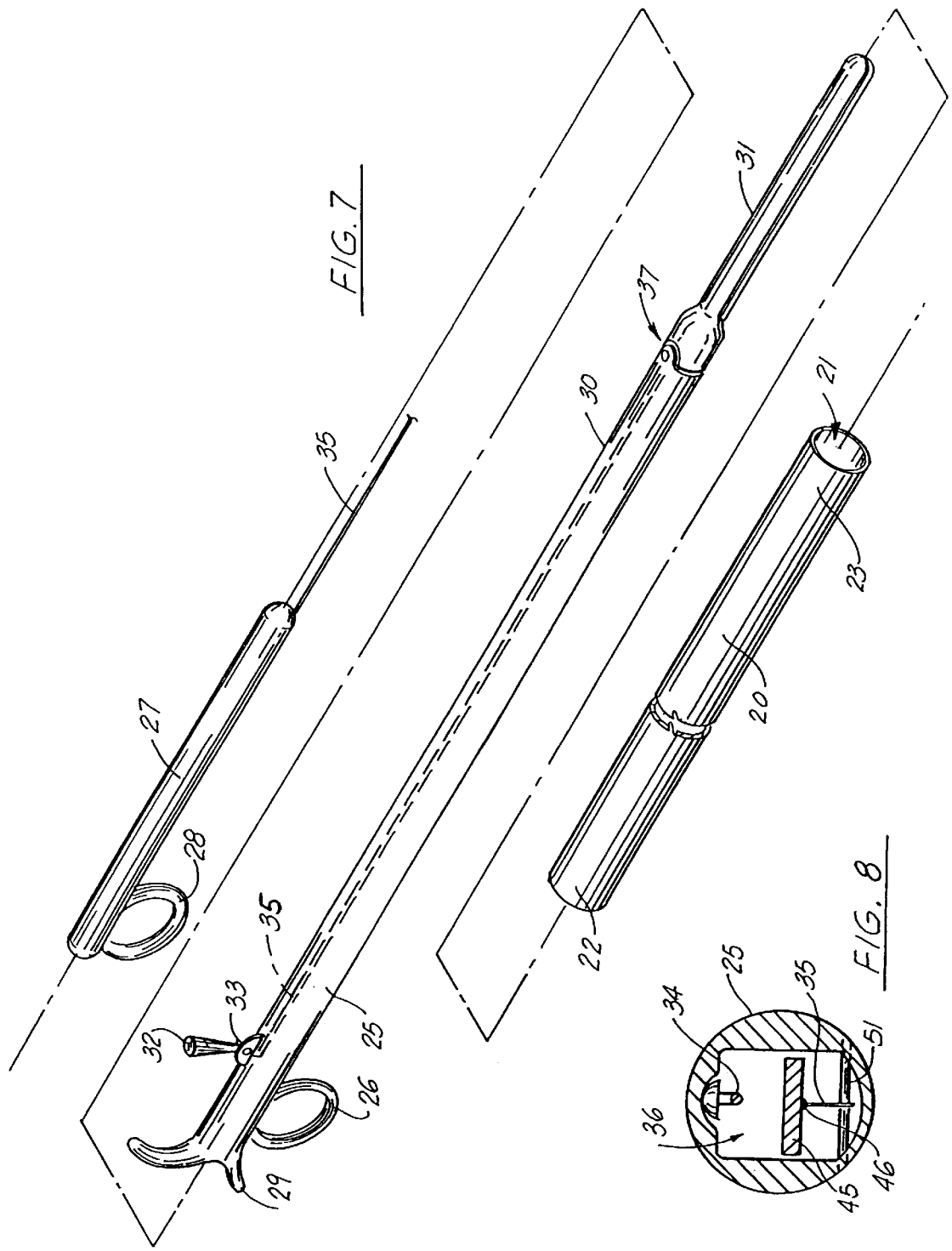

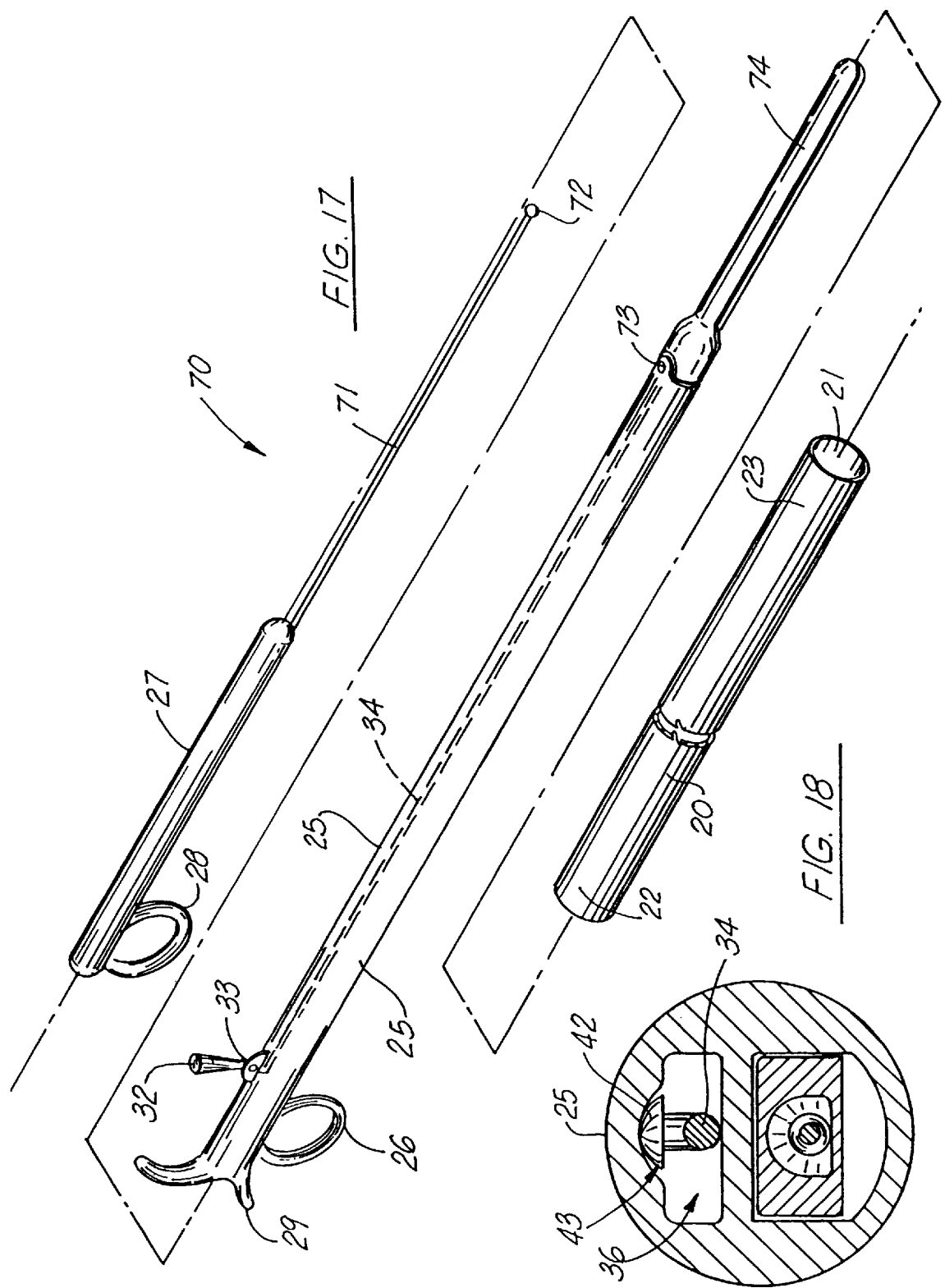

INSTRUMENTATION FOR LAPAROSCOPIC INSERTION AND APPLICATION OF SURGICAL SHEET MATERIAL

CROSS REFERENCE TO RELATED APPLICATIONS

This is a continuation-in-part of U.S. patent application Ser. No. 08/407,409, filed Mar. 17, 1995, now U.S. Pat. No. 5,503,623 which is incorporated herein by reference.

BACKGROUND OF THE INVENTION

1. Field of the Invention

The present invention relates to a method and apparatus for inserting and applying large or full size sheets of surgical sheet like material (such as absorbable adhesion barrier sheets) and other sheet like products in laparoscopic (endoscopic) surgery, wherein the sheet of material is furled into a roll and held in a first delivery tube, then routed through a second tube or "port" for positioning and dispensing within the abdominal cavity.

2. General Background

Surgery performed within the pelvis and abdomen by means of laparoscopy utilizes of one or more entry "ports" in varying size. The majority of sizes is in the range of five (5) millimeters to fifteen (15) millimeters. Each port consists of a tube with proximal and distal ends. A valve structure on the proximal end of the port member allows instruments to be passed through the abdominal wall while maintaining appropriate intra-abdominal $CO_2$ pressure.

While instruments pass easily through the associated port member and its valve structure, cloth-like sheets of surgical material, such as absorbable adhesion barrier and the like, do not readily pass through the port. At this time, most laparoscopic surgeons cut such sheet like material into small pieces and shove it through the port, a more difficult insertion and also causing a less efficient and restricted application.

One example of surgical sheet like material is an absorbable adhesion barrier product manufactured by Johnson and Johnson Medical, Inc. under the trademark "Interceed". Such an absorbable adhesion barrier is typically rectangular, measuring about three inches (3") wide and four inches (4") long. It is designed to be placed over surgical sites within that pelvis and abdomen.

Once placed on sites where surgery is performed, such a sheet like adhesion barrier helps in preventing development or recurrence of adhesions (a type of scarring) which can be painful and, in certain instances, dangerous. Currently, such a barrier (or sheet like material) is placed mostly by laparotomy (opened abdomen surgery). It is thus desirable to be able to efficiently place adhesion barrier sheets and similar sheet like surgical products into the abdomen laparoscopically, while making their proper placement easier and better. Placing anything laparoscopically into the abdomen is limited by the port member, from both a size standpoint and the valve structure, the latter being necessary to maintain intra-abdominal pressure.

In surgeries where large areas are involved and application of sheet like products is desirable, the largest sheet of the product needed should be utilized. This provides not only faster and more efficient use of surgical time but a better and more stable application as well.

The present instrument provides a system for laparoscopic use of large pieces or full size sheets of sheet like surgical material (such as absorbable adhesion barrier) and the like.

SUMMARY OF THE INVENTION

The present invention provides an instrumentation system for laparoscopic insertion and application of a surgical sheet like material such as absorbable adhesion barrier and the like. The method of the present invention comprises the grasping and furling of the sheet of material long wise along its border with a grasping instrument.

An instrument inserter tube or sheath is provided that is shorter in length then the grasping section. The grasping section extends through the inserter tube and protrudes beyond the distal end. The sheet of material is furled onto the grasping and furling section and drawn back ("backloaded") into the introducer.

A handle on the grasping instrument portion provides two finger grip positions that allow the surgeon to slide a cable (or pushrod) connected to one of the grasping elements (a movable member) back and forth so as to fix or release the sheet like material.

A lever positioned on top of the grasping portion of the instrument moves backward and forward to cause a mechanical articulation of the grasping element once inside the patient's abdomen to aid in placement on the desired surface.

The proposed method of furling the sheet like material causes it to be rolled up lengthwise and in such a configuration it occupies very little space. The present instrument system is designed to allow efficient furling in a compact space, easy insertion or passage through the abdominal wall port, and then unfurling and applying to the surgical site.

In the initial step of the method, a rectangular (e.g. 3"×4") piece of sheet like material is placed long wise in the grasping section of the instrument which is then rotated resulting in the sheet like material being furled. The next step is to slide this furled sheet backwards into the inserter sheath while it is being grasped. The backloaded, furled sheet, is now "ready". This sheet is held within a tube and the assembly is then passed through the laparoscopy port, a tubular member. The grasping portion is pushed forward through the port and into the patient's abdominal cavity. The sheet like material is then unfurled and applied, employing horizontal (left to right) articulation if needed.

A gasket-seal is located at the connection between the instrument frame and inserter tube portion outside the abdomen. This prevents CO2 gas in the abdomen from escaping.

There are a number of advantages of this instrument. The present invention provides a single intact reusable instrument, having a portion of the instrument being reusable and another portion being preferably disposable.

The present also invention provides an entirely disposable instrument with the ability to have prepackaged surgical products or simply providing the disposable instrument alone.

The same instrument system measurements could be altered in dimension so as to be utilized with other products with cloth-like and/or sheet like characteristics of different sizes and/or thickness.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 7 is an exploded perspective view of the preferred embodiment of the apparatus of the present invention;

FIG. 8 is a sectional view of the preferred embodiment of the apparatus of the present invention;

FIG. 17 is a perspective exploded view of a second alternate embodiment of the apparatus of the present invention;

FIG. 18 is a transverse cross-sectional view of the embodiment of FIG. 17;

DETAILED DESCRIPTION OF THE PREFERRED EMBODIMENT

Figure 4:
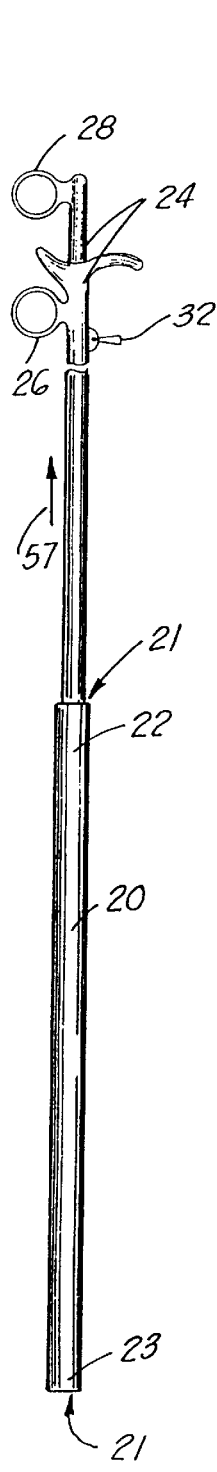
FIG. 4 is a side view of the preferred embodiment of the apparatus of the present invention showing the inserter instrument with a sheet of surgical material loaded in the distal end portion of the inserter instrument body.
Figure 5:
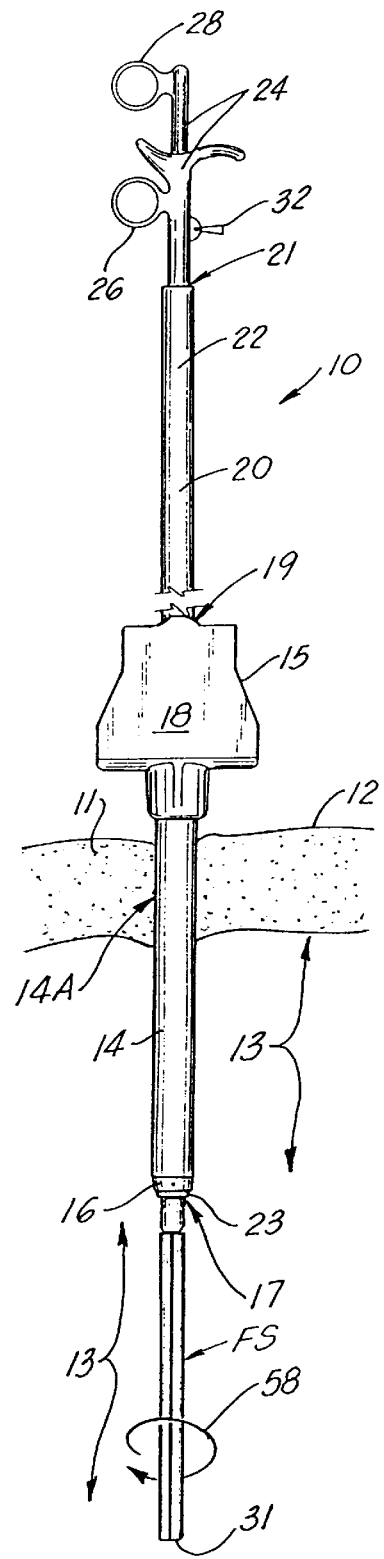
FIG. 5 is a schematic view illustrating placement of the apparatus of the present invention through a patient's abdominal wall and illustrating the method of the present invention.
Figure 6:
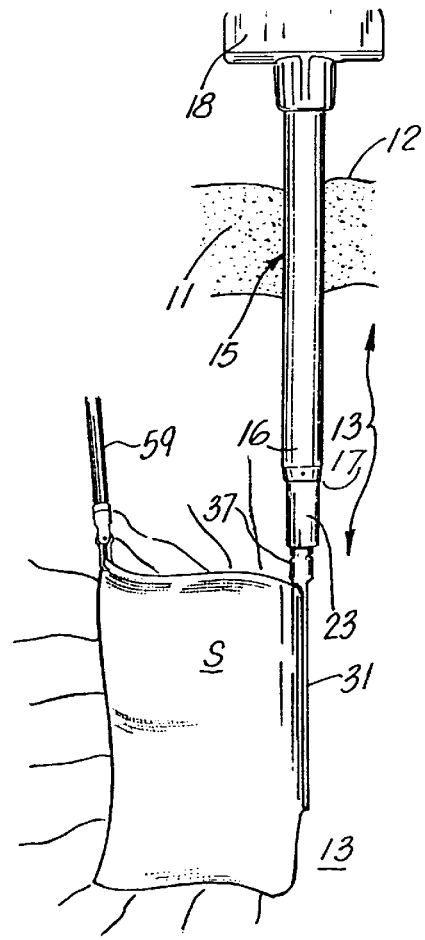
FIG. 6 is a side schematic view illustrating the method of the present invention.

FIGS. 1–6 illustrate the preferred embodiment of the apparatus of the present invention designated generally by the the numeral 10. Laparoscopy instrument 10 includes an elongated structure that can be placed through the abdominal wall 11 of a patient as shown in FIG. 5. Also shown in FIGS. 5 and 6 is the patient's skin 12 and the abdominal cavity 13 into which an inserter instrument portion 24 of the instrument 10 will be placed.

Tubular port 14 extends through an opening 14A formed with the tubular member 14 through the patient's abdominal wall 11. This procedure of placing a port in the abdominal wall 11 is per se known. In such a procedure, it is known in the art to inflate the abdomen to give the surgeon a better view of the surgical site. The tubular port 14 is a commercially available structure that includes a proximal end 15 and a distal end 16. The tubular port 14 provides an elongated open end cylindrical bore 17 so that the surgeon can communicate between the abdominal cavity 13 and the exterior of the patient. Cylindrical bore 17 is valved with valving member 18. The valving member 18 likewise provides a bore that is in communication with the cylindrical bore 17. Such a port 14 with its valving member 18 is sold commercially for use in laparoscopic surgery.

An elongated inserter tube member 20 is sized and shaped to fit the internal bore 17 of the tubular port 14. The tubular member 20 provides a generally cylindrical outer surface that is of an external diameter that is substantially the same as or slightly smaller than the internal diameter cylindrical bore 17. The bore 19 of valving member 18 is also generally cylindrically shaped to conform to the outer surface of tubular member 20. The inserter tube member 20 has a proximal end 22 and a distal end 23. The tubular member 20 has a uniform cylindrical bore 21 that is open ended.

An elongated inserter instrument 24 is comprised of external tubular member 25 and internal tubular member 27 (see FIG. 7). The external tubular member 25 has a handle 26 for manipulating it. Similarly, the internal tubular member 27 has a handle 28. The two handles 26, 28 are each in the form of a ring so that the surgeon can place one of his or her fingers through the handles 26, 28 for manipulating and sliding the member 27 relative to the member 25.

Figure 10:
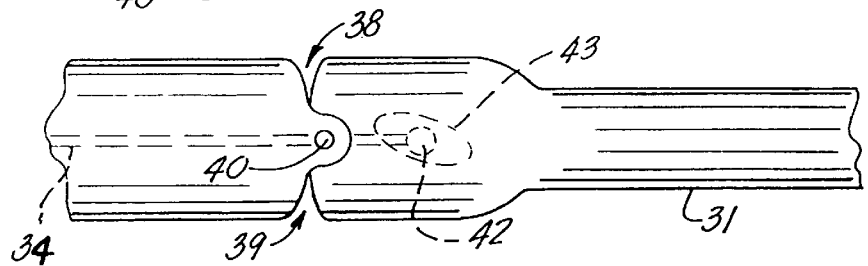
FIG. 10 is a top partial view of the preferred embodiment of the apparatus of the present invention.
Figure 11:
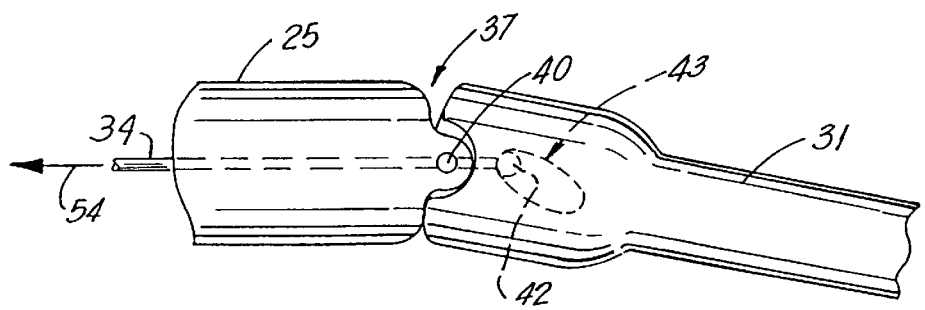
FIG. 11 is a top partial view of the preferred embodiment of the apparatus of the present invention illustrating an articulation of the distal end portion of the inserter instrument body.
Figure 12:
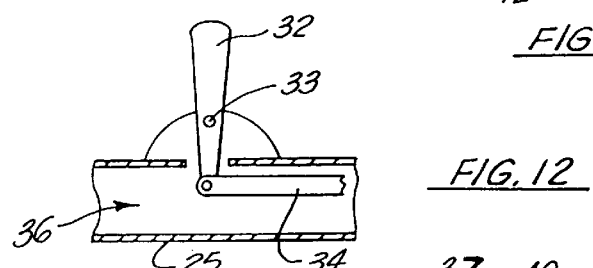
FIG. 12 is a fragmentary view of the lever portion of the preferred embodiment of the apparatus of the present invention.
Figure 13:
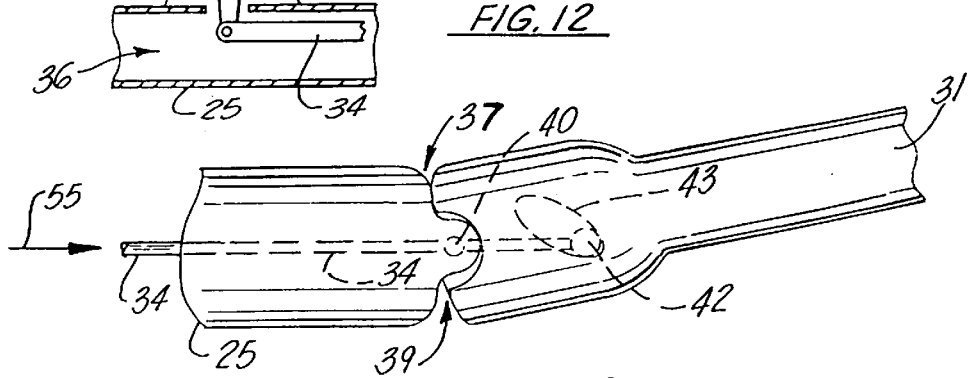
FIG. 13 is a fragmentary top view of the preferred embodiment of the apparatus of the present invention illustrating an articulation of the distal end portion of the inserter instrument.

External tubular member 25 has a proximal end 29 and a distal end 30. A grasping portion 31 is attached to the distal end 30 as shown in FIGS. 7 and 9–13. Lever 32 is pivotally attached to the proximal 29 end portion of external tubular member 25. Lever 32 is attached to pushrod 34 so that pivoting of lever 32 about its pivot 33 operates to extend or retract the pushrod relative to external tubular member 25. The lever 32 is used to articulate grasping portion 31 into multiple angular positions relative to the central longitudinal axis of the external tubular member 25 as illustrated in FIGS. 10–11 and 13.

A cable 35 is attached to internal tubular member 27. The cable 35 extends through a longitudinal bore 36 within external tubular member 25. As will be described more fully hereinafter, the cable 35 is moved by pulling or pushing the internal tubular member 27 relative to the external tubular member 25 using handles 26, 28.

An articulating joint 37 forms a connection between external tubular member 25 and grasping portion 31. As shown in FIGS. 10–11 and 13, a pair of spaces 38, 39 are provided at articulating joint 37 for allowing the grasping portion 31 to move left to right and angulate relative to the central longitudinal axis of external tubular member 25 as shown in FIGS. 10–11 and 13. A pinned connection 40 is formed at articulating joint 37 between the distal end 30 of external tubular member 25 and the grasping portion 31, allowing portion 31 to pivot upon tubular member 25.

Pushrod 34 includes an elbow section 41 that carries button 42. The button 42 fits in a recess 43. The recess 43 is formed on fixed member 44 of grasping portion 31. A moving member 45 is placed in close approximate to the fixed member 44. The moving member 45 travels away from the fixed member 44 when the cable 35 is pulled using lever 32. Cable 35 is attached at 46 to moving member 45. A coil spring 47 normally holds moving member 45 in face to face contact with fixed member 44. When the user pulls the internal tubular member 27 with handle 28, cable 35 pulls down underlying support 48 and moving member 45. A plurality of cable guides 49–51 are used to route the cable as shown in FIG. 9 to the under side of moving member 45 as shown.

Figure 9:
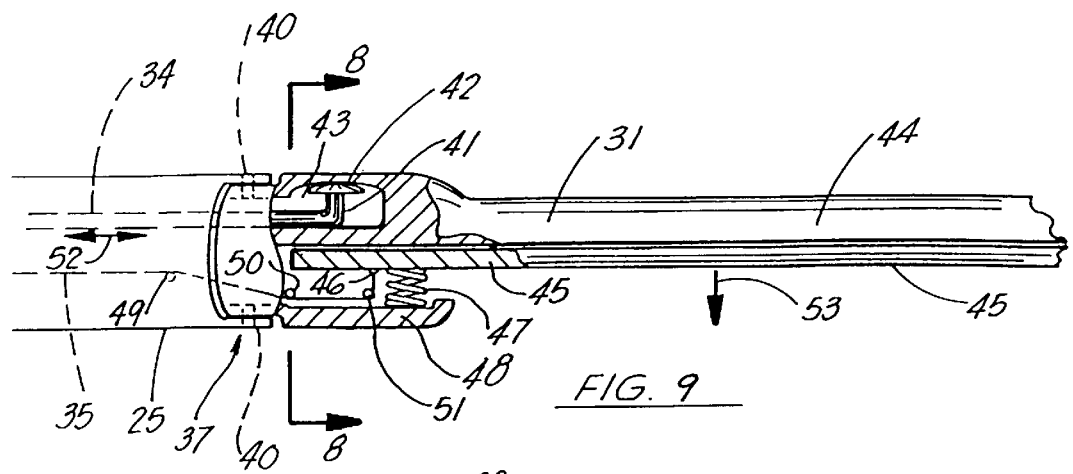
FIG. 9 is a fragmentary, partially cut-away view of the preferred embodiment of the apparatus of the present invention.

In FIG. 9, arrow 52 illustrates the movement of pushrod 34 fore and aft depending upon the surgeon's manipulation of lever 32. In FIG. 10, the pushrod 34 is a neutral position when the lever 32 is in an upright position, generally perpendicular to the central longitudinal axis of external tubular member 25 as shown in FIG. 7.

In FIG. 11, the surgeon has pulled the pushrod 34 as shown by arrow 54. This causes the button 42 to travel to the rear portion of recess 43 thereby pivoting grasping portion 31 relative to external tubular member 25. In FIG. 13, the surgeon has pushed the pushrod 34 using lever 32 as shown by the arrow 55. This causes the button 42 to travel to the forward portion of recess 43, thus pivoting the grasping portion 31 to the opposite angular position of that shown in FIG. 11. In this fashion, the surgeon can articulate or pivot the grasping portion 31 relative to the central longitudinal axis of the external tubular member 25.

Figure 1:
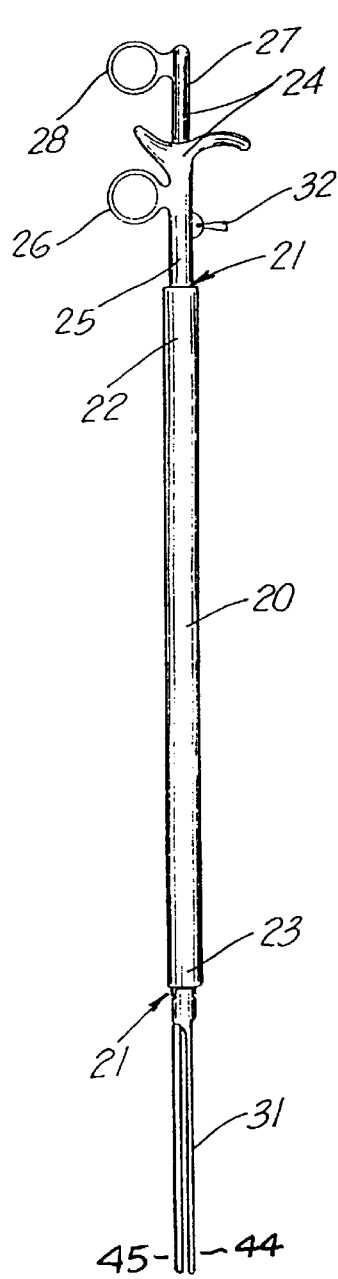
FIG. 1 is a side view of the preferred embodiment of the apparatus of the present invention.

In FIG. 9, arrow 53 designates a movement of moving member 45 away from fixed member 44. This is accomplished by pulling on the member 27 and its attached cable 35. Such a movement of member 45 in the direction of arrow 53 is used when either loading or releasing the sheet like member S to or from the instrument 10. The surgeon pulls the cable 35 to move member 45 away from member 44 producing a gap therebetween for application of an edge of sheet like member S thereto. In FIG. 1, the gap has been formed between members 44 and 45 so that the surgeon can insert an edge of a sheet of material S into the gap formed between the members 44 and 45.

Figure 2:
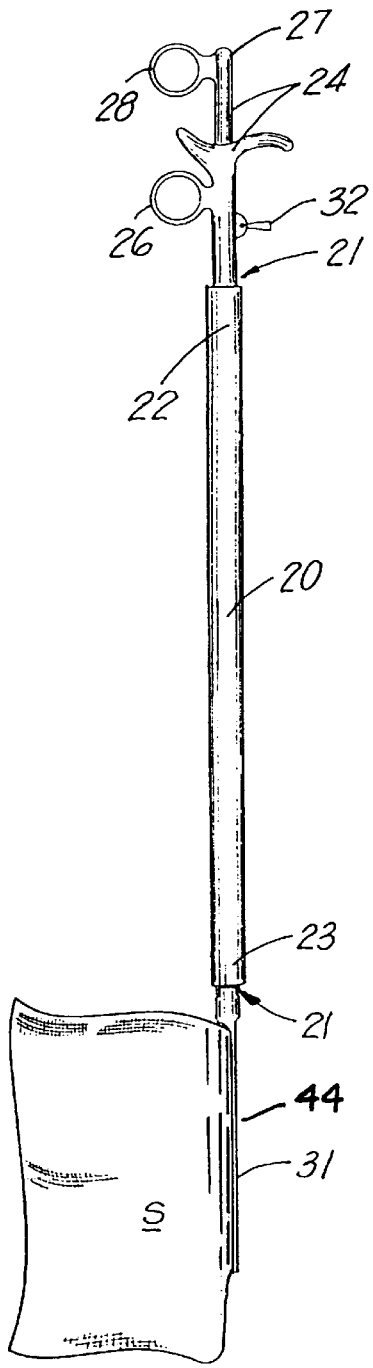
FIG. 2 is a side view of the preferred embodiment of the apparatus of the present invention illustrating the attachment of a sheet of surgical material thereto.
Figure 3:
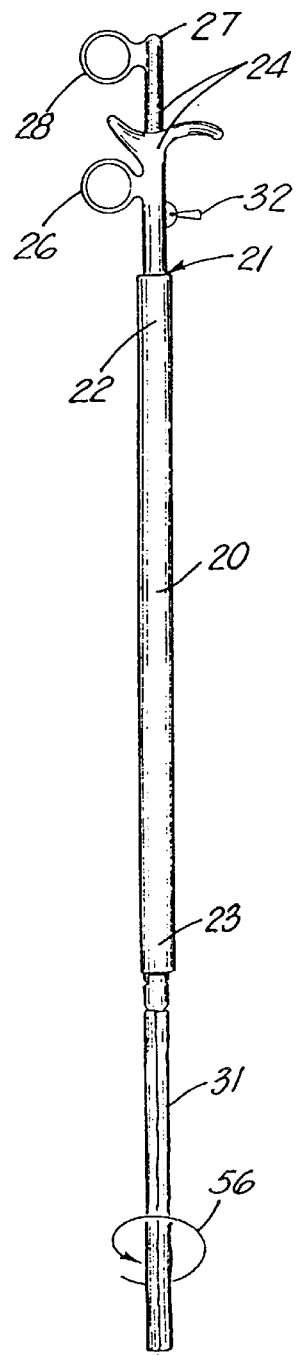
FIG. 3 is a side view of the preferred embodiment of the apparatus of the present invention showing the sheet of surgical material in a furled condition about the distal end of the inserter instrument body.

In FIG. 2, the sheet of material S has been placed in the gap between the member 44 and 45. The surgeon then releases the member 27 so that the spring 47 pushes the member 45 into close face to face contact with the member 44. This action clamps a selected edge of the sheet S between the members 44, 45 and allows the surgeon to furl the sheet S about grasping portion 31 as shown by the arrow 56 in FIG. 3.

In FIG. 4, arrow 57 indicates that the furled sheet S has been withdrawn into the bore of inserter tube 20. At this time, the sheet of material S has been furled about the grasping portion 31, and pulled into the bore 21. The combination of inserter tube 20, the sheet of material S, and the elongated inserter instrument 24 can now be inserted through tubular port member 14.

FIG. 5, the surgeon uses port 14 to place the sheet of material S into the patient's abdominal cavity 13. This is accomplished by routing the distal end 23 of inserter tube 20 and the contained inserter instrument 24 through the bore 19 of valving member 18 and then through the bore 17 of tubular port member 14. The surgeon projects the inserter tube 20 into the abdominal cavity 13 until the distal end 23 is positioned close to the distal end 16 of tubular port member 14 as shown in FIG. 5. The surgeon then holds the inserter tube 20, fixing its position relative to the tubular port 14. In the next step of the method, the surgeon forces the elongated inserter instrument 24 into the abdominal cavity by moving the elongated inserter instrument 24 relative to both inserter tube 20 and port 14 so that the grasping portion 31 and the furled sheet FS of material ar exposed inside the abdominal cavity 13.

In FIG. 5, the letters FS designate the furled sheet of material having been placed with the grasping portion 31 in the patient's abdominal cavity 13. The surgeon then rotates the elongated inserter instrument 24 as indicated by the arrow 58 in FIG. 5. This rotation unfurls the sheet of material S to the position shown in FIG. 6. A second port (such as member 14) can be used for placing a grasping instrument 59 into the abdominal cavity 13 for assisting the surgeon in application of the sheet of material S as illustrated in FIG. 6.

Figure 14:
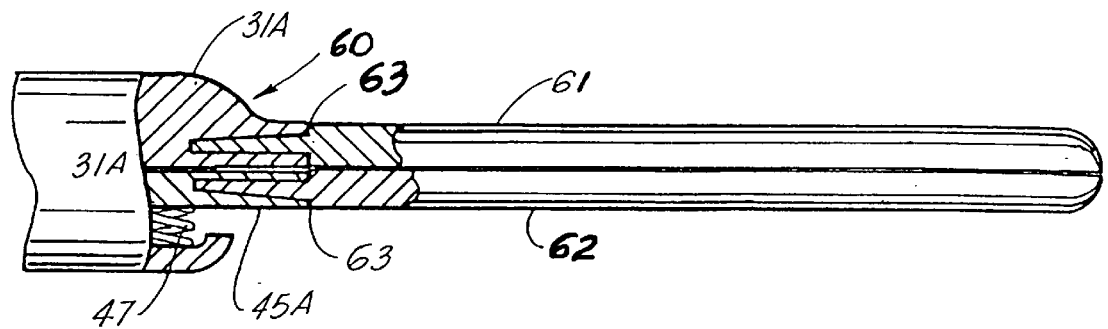
FIG. 14 is a partial, cut-away view of the distal end portion illustrating an alternative construction of the distal end portion of the inserter instrument.
Figure 15:
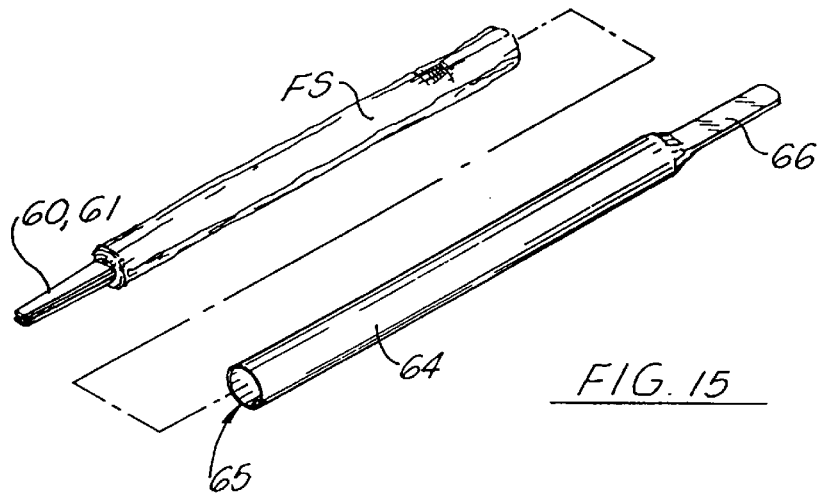
FIG. 15 is a fragmentary perspective view of the alternate construction of the distal end of the inserter instrument body.
Figure 16:
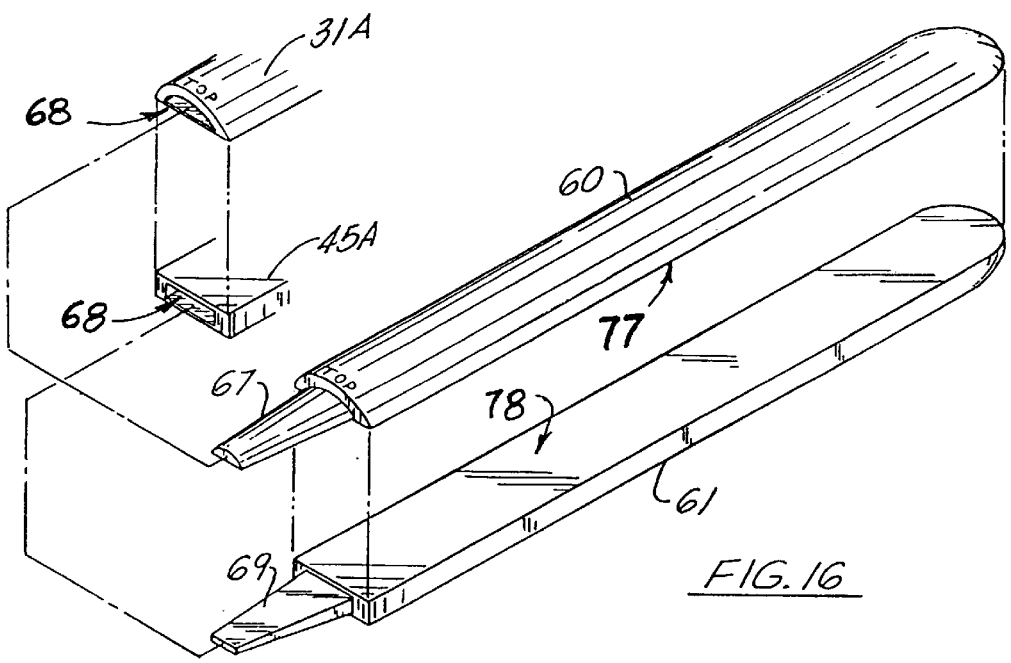
FIG. 16 is an exploded fragmentary view of the distal end portion of the inserter instrument body.

An alternate construction of the grasping portion is shown in FIGS. 14–16, designated as grasping portion 31A. Grasping portion 31A includes a removable connection designated as 60 in FIG. 14. Connection 60 is formed between grasping portion 31A and a pair of removable end 61 and grasping portion 31A. Removable end 62 is connection at joint 63B to moving member 45A.

In FIG. 15, a pre-packaged furled sheet FS of material is shown, furled about the removable ends 61, 62. The ends 61, 62 are pre-packaged with sheet S furled about the ends 61, 62. An edge of sheet S is grasped between end 61, 62. The furled sheet FS and end 62, 63 would be contained within the bore 65 of an elongated disposable sleeve 64. The sleeve 64 provides a pull tab 66 so that the user can install the furled sheet FS avoiding premature unfurling by simply holding and manipulating the sleeve 64. After the removable ends 61, 62 are installed by perfecting a connection at the joints 63A, 63B and backloading the furled sheet FS into sleeve 20, the surgeon then pulls on the pull tab 66 to remove the sleeve 64 so that the surgery can proceed.

In FIG. 16, removable end 61 provides a projection 67 that mates with a correspondingly shaped socket 68 of grasping portion 31A. Similarly, the moving member 45A provides a socket 68 that forms a connection with projecting portion 69 of end 62. The end members 61, 62 each provide correspondingly sized and shaped flat surfaces 77, 78 that abut in face to face relation when the coil spring 47 forces members 45A, and 31 and 61, 62 together.

The connection between projections 67, 69 and socket 68 and 70 can be a wedge lock or taper lock type connection to ensure a tight fit. In the embodiment of FIGS. 14–16, the removable ends 61, 62 and the furled sheet FS and sleeve 64 could be in a presterlized blister pack for example.

FIGS. 17–20 show a second alternate embodiment of the apparatus of the present invention designated generally by the numeral 70. Instrument 70 includes an external tubular member 25 that is constructed in accordance with the preferred embodiment of FIGS. 1–13. The internal member 27 is constructed generally in accordance with the preferred embodiment. However, the internal tubular member 27 carries a pushrod 71 instead of cable 35.

Pushrod 71 has a distal end in the form of a spherical member or ball 72. The member 25 has a proximal end 29 and a central longitudinal bore that accepts the internal tubular member 27. This allows the member 27 to slide within the bore of the member 25. Handle 26 and 28 enable a surgeon to grip and manipulate instrument 70 and to slide member 27 relative to member 25.

As with the preferred embodiment, the embodiment of FIG. 17–20 includes an external tubular member 25 having a hollow bore that accepts pushrod 34. The pushrod 34 is attached to lever 32. The lever 32 affixes at pivot 33 to external tubular member 25.

In the embodiment of FIGS. 17–20, a pivotal connection 73 is formed between the member 25 and grasping portion 74. Lever 32 can be pivoted about its pivot 33 in order to extend or retract pushrod 34. As with the preferred embodiment, the pushrod 34 has an elbow section 41 and a button portion 42. As with the preferred embodiment, the button 42 occupies recess 43.

The pushrod 34 and its button 42 can be used to articulate grasping portion 74 about pivot 73 relative to external tubular member 25. This pivoting action of grasping portion 74 relative to member 25 operates the same as the pivoting that was shown and described in FIGS. 10–13 in the description of the preferred embodiment.

Figure 19:
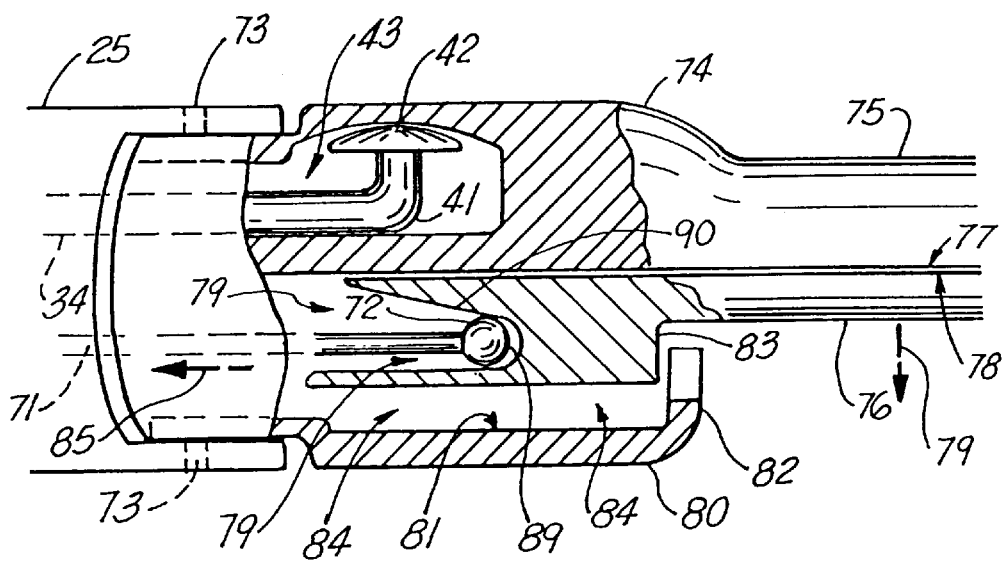
FIG. 19 is a partial, sectional elevational view of the embodiment of FIGS. 17 and 18.
Figure 20:
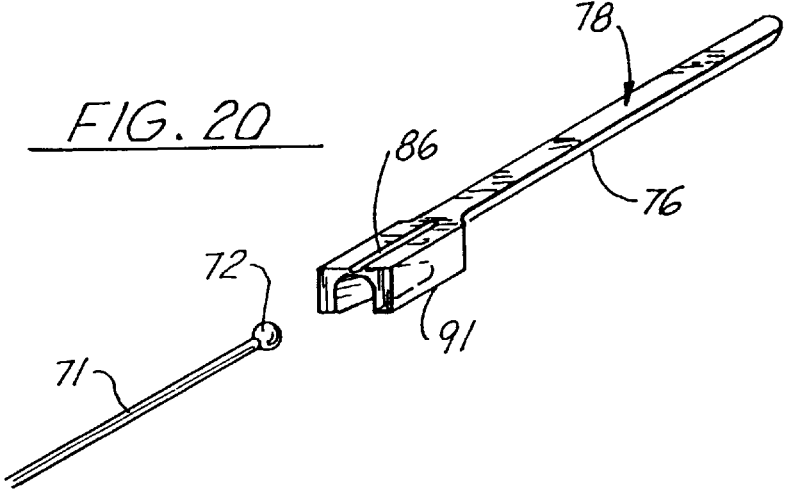
FIG. 20 is a partial perspective view of the embodiment of FIGS. 17–19.

In FIG. 19, pushrod 71 is shown having a distal end with ball 72 that fits socket 79. The socket 79 is partially cone shaped, also having a hemispherical portion 89 that registers against ball 72. Lower jaw 76 is in a closed position when ball 72 moves forward and engages the hemispherical portion 89 of socket 79. This pushes the lower jaw 76 into engagement with the upper jaw 75.

The jaw 76 has an inclined surface 90 that is engaged by the ball 72 as the pushrod 71 moves forward. Jaw 76 has a flat surface 83 that engages shoulder 82 of undersupport 80. The undersupport 80 has a flat surface 81 that receives the enlarged proximal section 91 of lower jaw 76.

In order to open the jaws 75, 76 the user pulls handle 28 of member 27. This also places pushrod 71 in tension, pulling the ball 72 away from the hemispherical portion 89 of socket 79. As ball 72 is withdrawn (see arrow 85 in FIG. 19), lower jaw 76 drops in the direction of arrow 79 due to its own weight. Shoulder 82 engages the flat surface 83 of enlarged portion 91, holding the jaw 76 in its operative position adjacent jaw 75. There is enough of a gap 84 in between the enlarged portion 91 and the undersupport 80 so that the lower jaw 76 moves away from the upper jaw 75 forming a gap therebetween to hold sheet S.

The external member 25 and jaws 75, 76 fit within the bore 21 of inserter tube 20. The member 25 is longer than tube 20 so that jaws 75, 76 can be placed inside the patient's abdominal cavity while the surgeon is holding handles 26, 28 and manipulating lever 32. This allows jaws 26, 28 to be opened and closed inside the patient's abdominal cavity. This allows the jaws 75, 76 to articulate about pivot 73. The jaws 75, 76 can be opened and closed, even when the jaws are articulated to the left or to the right of the central longitudinal axis of member 25.

As with the preferred embodiment, a sheet S of surgical material can be gripped by jaws 75, 76 and then furled about the jaws 75, 76 for entry into inserter tube 20. The jaws 75, 76 preferably present a generally cylindrically shaped outer surface when the jaws 75, 76 are closed. The inner surface of the jaws 75, 76 could be smooth for delicate materials which might break with a serrated gripper, and serrated for slipperier materials which would not break with a gripper having serrations. Serrations of various coarseness could be used (the slipperier and more tough the material to be gripped, the larger the serrations).

Figure 21:
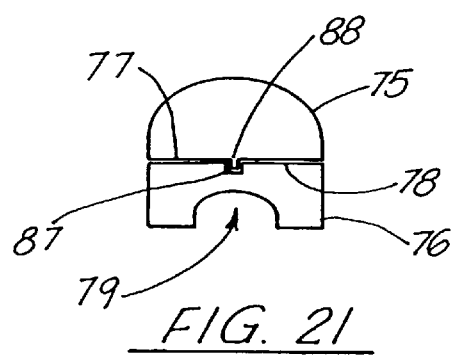
FIG. 21 is a fragmentary sectional view of the third embodiment of the apparatus of the present invention illustrating the upper and lower jaws.
Figure 22:
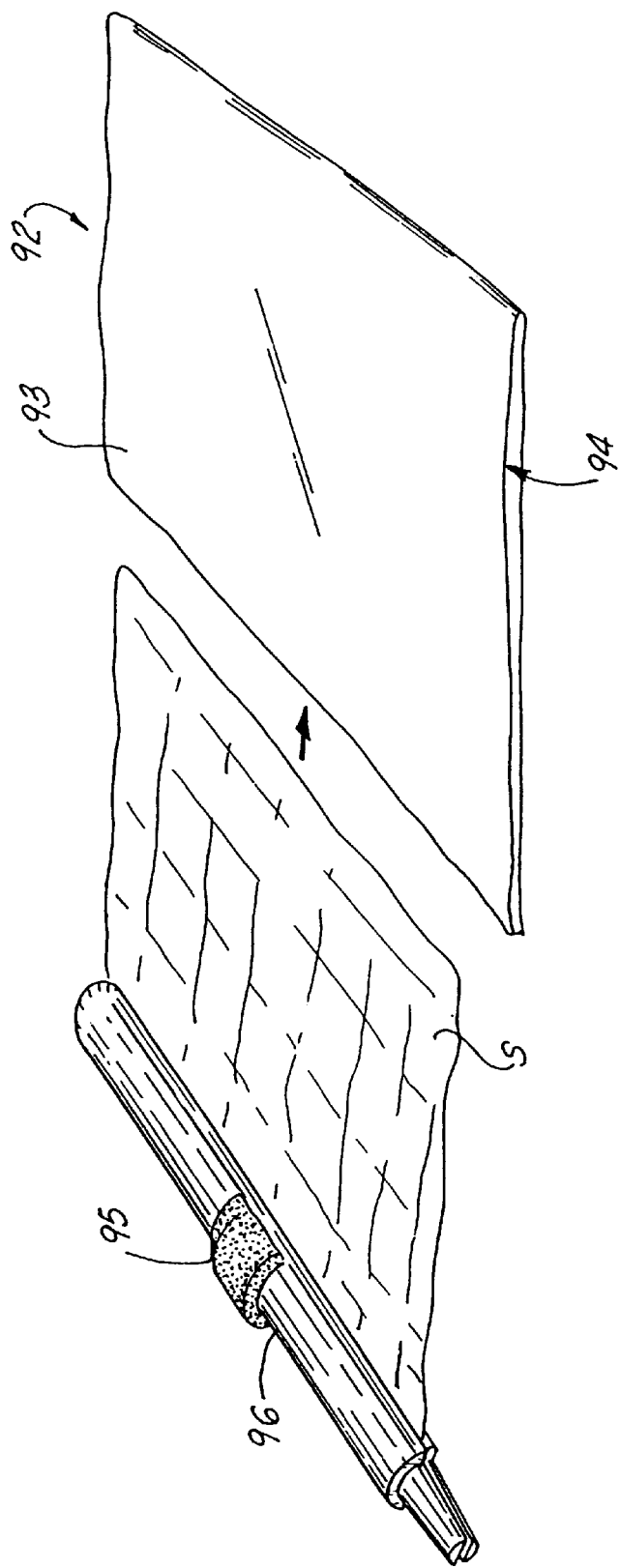
FIG. 22 is a perspective view of a fourth embodiment of the apparatus of the present invention.

In FIG. 21, a fourth embodiment of the apparatus of the present invention is shown, designated as 92 and illustrating an alternate jaw and surgical sheet arrangement and pre-packaging. To package the surgical material S with the disposable jaws 75, 76 rolling (as shown in FIG. 15) of the material S is usually easier and probably cheaper. However, rolling will generally not work well when the material S has a "memory" which might hinder unrolling during surgery, then it is preferably packaged flat in the interior 94 of envelope 93 (see FIG. 22). Plastic clip 95 shown in FIG. 22 is resilient and provides a recess 96 that conforms to the shape of the outer surface of the assembled upper jaw 75 and lower jaw 76. Plastic clip 95 holds jaws 75 and 76 together and secures the surgical sheet S in place. Plastic clip 95 pulls off after the jaws 75, 76 are snapped onto instrument in surgery as with the embodiment of FIGS. 14–16.

The following table lists the parts numbers and parts descriptions as used herein and in the drawings attached hereto.

| Part Number | Description |
| --- | --- |
| | PARTS LIST |
| 10 | laparoscopy instrument |
| 11 | abdominal wall |
| 12 | skin |
| 13 | abdominal cavity |
| 14 | tubular port |
| 15 | proximal end |
| 16 | distal end |
| 17 | cylindrical bore |
| 18 | valving member |
| 19 | bore |
| 20 | inserter tube |
| 21 | cylindrical bore |
| 22 | proximal end |
| 23 | distal end |
| 24 | inserter instrument |
| 25 | external tubular member |
| 26 | handle |
| 27 | internal tubular member |
| 28 | handle |
| 29 | proximal end |
| 30 | distal end |
| 31 | grasping portion |
| 31A | grasping portion |
| 32 | lever |
| 33 | pivot |
| 34 | pushrod |
| 35 | cable |
| 36 | longitudinal bore |
| 37 | articulating joint |
| 38 | space |
| 39 | space |
| 40 | pinned connection |
| 41 | elbow section |
| 42 | button |
| 43 | recess |
| 44 | fixed member |
| 45 | moving member |
| 46 | attachment |
| 47 | coil spring |
| 48 | underlying support |
| 49 | cable guide |
| 50 | cable guide |
| 51 | cable guide |
| 52 | arrow |
| 53 | arrow |
| 54 | arrow |
| 55 | arrow |
| 56 | arrow |
| 57 | arrow |
| 58 | arrow |
| 59 | grasping tool |
| 60 | removable connection |
| 61 | removable end |
| 62 | removable end |
| 63A | joint |
| 63B | joint |
| 64 | sleeve |
| 65 | cylindrical bore |
| 66 | pull tab |

-continued

PARTS LIST

| Part Number | Description |
|---|---|
| 67 | projection |
| 68 | socket |
| 69 | projection |
| 70 | instrument |
| 71 | cable |
| 72 | ball |
| 73 | pivot |
| 74 | grasping portion |
| 75 | upper jaw |
| 76 | lower jaw |
| 77 | flat surface |
| 78 | flat surface |
| 79 | socket |
| 80 | undersupport |
| 81 | flat surface |
| 82 | shoulder |
| 83 | flat surface |
| 84 | gap |
| 85 | arrow |
| 86 | arrow |
| 87 | groove |
| 88 | keyway |
| 89 | hemispherical |
| 90 | inclined surface |
| 91 | enlarged portion |
| 92 | jaw assembly |
| 93 | envelope |
| 94 | interior |
| 95 | plastic clip |
| S | sheet |
| FS | furled sheet |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A laparoscopy instrument for inserting a surgical sheet article into a patient's abdomen comprising;
   a) an instrument body that includes a first member having a bore, a proximal end portion and a distal end portion;
   b) a second member that slides in the bore of the first member between first and second positions;
   c) a set of longitudinally extended jaws positioned at the distal end of the second member, said jaws being active jaws that are operable between open and closed positions, the jaws having respective gripping surfaces that abut in the closed position;
   d) a tubular cannula through which the instrument body can be inserted during a surgical laparoscopic procedure so that the distal end of the instrument body, the jaws, and a gripped surgical sheet article can communicate with the patient's abdominal cavity when the instrument body is inserted through the cannula;
   e) wherein the jaws abut along substantially their entire length enabling them to grip and support the surgical sheet article, and of a shape that enables the sheet article to be furled about the jaws inside the bore of the first member;
   f) the second member defining an operator with a handle that can be manipulated by a surgeon at its proximal end portion for enabling an opening and closing of the jaws;
   g) wherein the jaws have a cross section that fits inside the bore of the first member that enlarges when the jaws open beyond the distal end of the bore of the first member so that the sheet material can be released distally of the first member by opening the jaws; and
   h) wherein the second member is longer than the first member, enabling the jaws and furled sheet article to be discharged from and positioned beyond the distal end of the first member when the handle is manipulated by a surgeon to a position next to the proximal end of the first member so that the sheet can be unfurled and released from the jaws by manipulation of the handle to open the jaws after the jaws and furled sheet are positioned beyond the distal end of the first member and within the patient's abdominal cavity without obstruction by the first member during the unfurling of the sheet.

2. The surgical instrument of claim 1 wherein the jaws are movably connected to the instrument body so that the jaws can articulate with respect to the instrument body.

3. The surgical instrument of claim 1 wherein the jaws are movably connected to the instrument body so that the jaws can articulate with respect to the instrument body, and a lever mounted on the proximal end of the instrument body enables the surgeon to manipulate the jaws into multiple positions.

4. The laparoscopy instrument of claim 3 wherein the jaws pivot about a pivotal axis that is generally perpendicular to the central longitudinal axis.

5. The surgical instrument of claim 1 wherein the instrument body is an elongated linear member that has a central longitudinal axis.

6. The surgical instrument of claim 1 wherein the jaws each have flat surfaces that abut to grip the sheet therebetween.

7. A laparoscopy instrument for inserting a surgical sheet article into a patient's abdomen comprising:
   a) an instrument body that includes a first member having a bore, a proximal end portion and a distal end portion;
   b) a second member that slides in the bore of the first member between first and second positions;
   c) a set of jaws positioned at the distal end of the first member, said jaws being active jaws, operable between open and closed positions, the jaws being extended longitudinally, each jaw having a gripping surface that abuts the other in the closed position, the jaws being of a length to support the sheet article along a substantial portion of one of its sides;
   d) a tubular cannula through which the instrument body can be inserted during a surgical laparoscopic procedure so that the distal end of the instrument body and the jaws can communicate with the patient's abdominal cavity when the instrument body is inserted through the cannula;
   e) the second member defining an operator with a handle that can be manipulated by a surgeon, the handle positioned at the proximal end of the instrument body for opening and closing the jaws; and
   f) wherein the jaws are pivotally connected to the instrument body so that the jaws can pivot with respect to the instrument body.

8. A laparoscopy instrument for inserting a surgical sheet article into a patient's abdomen comprising:
   a) an instrument body that includes a first member having a bore, a proximal end portion and a distal end portion;
   b) a second member that slides in the bore of the first member between first and second positions;
   c) a set of jaws positioned at the distal end of the first member, said jaws being active jaws, operable between open and closed positions, the jaws being extended longitudinally, each jaw having a gripping surface that abuts the other in the closed position, the jaws being of a length to support the sheet article along a substantial portion of one of its sides;

d) a tubular cannula through which the instrument body can be inserted during a surgical laparoscopic procedure so that the distal end of the instrument body and the jaws can communicate with the patient's abdominal cavity when the instrument body is inserted through the cannula;

e) the second member defining an operator with a handle that can be manipulated by a surgeon, the handle positioned at the proximal end of the instrument body for opening and closing the jaws;

f) the jaws are movably connected to the instrument body so that the jaws can articulate with respect to the instrument body, and a lever mounted on the proximal end of the instrument body enables the surgeon to manipulate the jaws into multiple positions; and g) wherein the jaws are pivotally connected to the instrument body so that the jaws can pivot with respect to the instrument body, and further comprising a lever that is operable by the surgeon to move the jaws into multiple positions as the jaws pivot relative to the instrument body.

9. A laparoscopy instrument for inserting a surgical sheet article into a patient's abdomen comprising:

a) an instrument body that includes a first member having a bore, a proximal end portion and a distal end portion;

b) a second member that slides in the bore of the first member between first and second positions;

c) a set of jaws positioned at the distal end of the first member, said jaws being active jaws, operable between open and closed positions, the jaws being extended longitudinally, each jaw having a gripping surface that abuts the other in the closed position, the jaws being of a length to support the sheet article along a substantial portion of one of its sides;

d) a tubular cannula through which the instrument body can be inserted during a surgical laparoscopic procedure so that the distal end of the instrument body and the jaws can communicate with the patient's abdominal cavity when the instrument body is inserted through the cannula;

e) the second member defining an operator with a handle that can be manipulated by a surgeon, the handle positioned at the proximal end of the instrument body for opening and closing the jaws; and f) a pushrod having a distal end that engages one of the jaws, the pushrod being operable to open and close the one jaw relative to the other jaw.

10. The surgical instrument of claim 9 further comprising a ball that fits the distal end of the pushrod and a socket on the jaw for receiving the ball.

11. A laparoscopy instrument for inserting a surgical sheet article into a patient's abdomen comprising:

a) an instrument body that includes a first member having a bore, a proximal end portion and a distal end portion;

b) a second member that slides in the bore of the first member between first and second positions;

c) a set of jaws positioned at the distal end of the first member, said jaws being active jaws, operable between open and closed positions, the jaws being extended longitudinally, each jaw having a gripping surface that abuts the other in the closed position, the jaws being of a length to support the sheet article along a substantial portion of one of its sides;

d) a tubular cannula through which the instrument body can be inserted during a surgical laparoscopic procedure so that the distal end of the instrument body and the jaws can communicate with the patient's abdominal cavity when the instrument body is inserted through the cannula;

e) the second member defining an operator with a handle that can be manipulated by a surgeon, the handle positioned at the proximal end of the instrument body for opening and closing the jaws; and f) a pushrod that extends through the first member to engage the jaws, movement of the pushrod effecting a pivotal movement of the jaws when the jaws are in an open or in a closed position.

12. A laparoscopy instrument for inserting a surgical sheet article into a patient's abdomen comprising:

a) an elongated instrument body that includes an elongated tubular member having a longitudinal bore, a proximal end portion and a distal end portion;

b) an elongated operator member that slides in the bore of the first member between first and second positions;

c) a set of longitudinally extended jaws positioned at the distal end of the second member, said jaws being active jaws that are operable between open and closed positions, the jaws having respective gripping surfaces that abut in the closed position;

d) a tubular cannula having a cannula bore through which the instrument body can be inserted during a surgical laparoscopic procedure, the instrument body being longer than the cannula bore so that the distal end of the instrument body, the jaws, and the gripped surgical sheet article can communicate with the patient's abdominal cavity when the instrument body is inserted through the cannula;

e) wherein the jaws abut along substantially their entire length enabling them to grid and support the surgical sheet article, and of a shape that enables the sheet article to be furled about the jaws inside the bore of the first member;

f) the operator member having a handle that can be manipulated by a surgeon, the handle positioned at the proximal end of the instrument body for enabling a surgeon to move the operator for opening and closing the jaws; and g) wherein the jaws and furled sheet article can be discharged from and positioned beyond the distal end of the instrument body so that the sheet can be unfurled and released from the jaws after the jaws and furled sheet are positioned beyond the distal end of the instrument body and within the patient's abdominal cavity without obstruction by the first member during the unfurling of the sheet.

13. The laparoscopy instrument of claim 12 further comprising a handle at the proximal end for manipulating the instrument body.

14. The laparoscopy instrument of claim 13 wherein the jaws open and close in a plane and the jaw articulation axis lies in said plane.

15. The laparoscopy instrument of claim 13 wherein the outer surfaces of the jaws define a generally cylindrical shape.

16. A laparoscopy instrument for inserting a surgical sheet article into a patient's abdomen comprising:

a) an elongated instrument body that includes an elongated tubular member having a longitudinal bore, a proximal end portion and a distal end portion;

b) an elongated operator member that slides in the bore of the first member between first and second positions;

c) a set of jaws positioned at the distal end of the tubular member, said jaws being active jaws, operable between open and closed positions, the jaws being extended longitudinally, the jaws having respective gripping surfaces that abut in the closed position, the jaws being of a length to grip and support the surgical sheet article and of a shape that enables the sheet article to be furled about the jaws;

d) a tubular cannula having a cannula bore through which the instrument body can be inserted during a surgical laparoscopic procedure, the instrument body being longer than the cannula bore so that the distal end of the instrument body, the jaws, and the gripped surgical sheet article can communicate with the patient's abdominal cavity when the instrument body is inserted through the cannula;

e) the operator member having a handle that can be manipulated by a surgeon, the handle positioned at the proximal end of the instrument body for enabling a surgeon to move the operator for opening and closing the jaws;

f) wherein the jaws and furled sheet article can be discharged from the distal end of the first member so that the sheet can be unfurled and released from the jaws beyond the distal end of the first member and within the patient's abdominal cavity; and g) wherein the jaws are between about two and five (2–5) inches in length.

17. A laparoscopy instrument for inserting a surgical sheet article into a patient's abdomen comprising:

a) an elongated instrument body that includes an elongated tubular member having a longitudinal bore, a proximal end portion and a distal end portion;

b) an elongated operator member that slides in the bore of the first member between first and second positions;

c) a set of jaws positioned at the distal end of the tubular member, said jaws being active jaws, operable between open and closed positions, the jaws being extended longitudinally, the jaws having respective gripping surfaces that abut in the closed position, the jaws being of a length to grip and support the surgical sheet article and of a shape that enables the sheet article to be furled about the jaws;

d) a tubular cannula having a cannula bore through which the instrument body can be inserted during a surgical laparoscopic procedure, the instrument body being longer an the cannula bore so that the distal end of the instrument body, the jaws, and the gripped surgical sheet article can communicate with the patient's abdominal cavity when the instrument body is inserted through the cannula;

e) the operator member having a handle that can be manipulated by a surgeon, the handle positioned at the proximal end of the instrument body for enabling a surgeon to move the operator for opening and closing the jaws;

f) wherein the jaws and furled sheet article can be discharged from the distal end of the first member so that the sheet can be unfurled and released from the jaws within the patient's abdominal cavity; and g) wherein the second member includes a pushrod that extends to the jaws.

18. A laparoscopy instrument for inserting a surgical sheet article into a patient's abdomen comprising:

a) an elongated instrument body that includes an elongated tubular member having a longitudinal bore, a proximal end portion and a distal end portion;

b) elongated operator member that slides in the bore of the first member between first and second positions;

c) a set of jaws positioned at the distal end of the tubular member, said jaws being active jaws, operable between open and closed positions, the jaws being extended longitudinally, the jaws having respective gripping surfaces that abut in the closed position, the jaws being of a length to grip and support the surgical sheet article and of a shape that enables the sheet article to be furled about the jaws;

d) a tubular cannula having a cannula bore through which the instrument body can be inserted during a surgical laparoscopic procedure, the instrument body being longer than the cannula bore so that the distal end of the instrument body, the jaws, and the gripped surgical sheet article can communicate with the patient's abdominal cavity when the instrument body is inserted through the cannula;

e) the operator member having a handle that can be manipulated by a surgeon, the handle positioned at the proximal end of the instrument body for enabling a surgeon to move the operator for opening and closing the jaws;

f) wherein the jaws and furled sheet article can be discharged from the distal end of the first member so that the sheet can be unfurled and released from the jaws within the patient's abdominal cavity; and g) wherein the second member includes a pushrod with an attachment that extends to and from a connection with a first one of the jaws, the other jaw being fixed relative to the first jaw.

19. A laparoscopy instrument for inserting a surgical sheet article into a patient's abdomen comprising:

a) an elongated instrument body that includes an elongated tubular member having a longitudinal bore, a proximal end portion and a distal end portion;

b) an elongated operator member that slides in the bore of the first member between first and second positions;

c) a set of jaws positioned at the distal end of the tubular member, said jaws being active jaws, operable between open and closed positions, the jaws being extended longitudinally the jaws having respective gripping surfaces that abut in the closed position, the jaws being of a length to grip and support the surgical sheet article and of a shape that enables the sheet article to be furled about the jaws;

d) a tubular cannula having a cannula bore through which the instrument body can be inserted during a surgical laparoscopic procedure, the instrument body being longer than the cannula bore so that the distal end of the instrument body, the jaws, and the gripped surgical sheet article can communicate with the patient's abdominal cavity when the instrument body is inserted through the cannula;

e) the operator member having a handle that can be manipulated by a surgeon, the handle positioned at the proximal end of the instrument body for enabling a surgeon to move the operator for opening and closing the jaws;

f) wherein the jaws and furled sheet article can be discharged from the distal end of the first member so that the sheet can be unfurled and released from the jaws within the patient's abdominal cavity; and g) a pivot at the distal end of the instrument body, said pivot enabling the jaws to articulate about an articulation axis.

20. A laparoscopy instrument for inserting a surgical sheet article into a patient's abdomen comprising:

a) an instrument body with a proximal end portion and a distal end portion;

b) a set of jaws positioned at the distal end of the instrument body, said jaws being active jaws, operable between open and closed positions, the jaws having respective gripping surfaces that abut along substantially their entire length in the closed position, the jaws being of a length of at least three to four (3–4) inches to grip and support the surgical sheet article and of a shape that enables the sheet article to be furled about the jaws; and c) a tubular cannula with a bore through which the instrument body and jaws can be inserted during a surgical laparoscopic procedure so that the distal end of the instrument body, the jaws, and the gripped surgical sheet article can communicate with the patient's abdominal cavity when the instrument body is inserted through and beyond the cannula bore;

d) an operator with a handle that can be manipulated by a surgeon, the handle positioned at the proximal end of the instrument body for opening and closing the jaws;

e) the instrument body being elongated enough so that the surgeon can position the jaws in the patient's abdominal cavity and wherein the jaws can be opened and closed with the operator when so positioned inside the patient's abdominal cavity; and f) wherein the jaws and furled sheet article can be discharged from and positioned beyond the distal end of the first member so that the sheet can be unfurled and released from the jaws after the jaws and furled sheet are positioned beyond the distal end of the first member and within the patient's abdominal cavity without obstruction by the first member during the unfurling of the sheet.

21. The instrument of claim 20 further comprising an envelope that holds the surgical sheet like article.

22. The instrument of claim 20 wherein the sheet-like article has a memory that prevents or hinders unrolling during surgery and further comprising an envelope that packages the sheet like article in a flat position.

23. The instrument of claim 22 further comprising a clamp that holds the jaws in a gripping position wherein the jaws are attached to the sheet like article.

* * * * *